United States Patent [19]
Rushing

[11] Patent Number: 6,144,024
[45] Date of Patent: Nov. 7, 2000

[54] DIGITAL DENSITOMETER USING VOLTAGE-CONTROLLED OSCILLATOR, COUNTER, AND LOOK-UP TABLE

[76] Inventor: Allen J. Rushing, Eastman Kodak Company 343 State St., Rochester, N.Y. 14650

[21] Appl. No.: 09/183,509

[22] Filed: Oct. 30, 1998

[51] Int. Cl.[7] .................................................. G01N 21/00
[52] U.S. Cl. .................................... 250/214 DC; 356/445
[58] Field of Search ..................... 250/214 DC; 327/514; 356/432–435, 445, 448

[56] References Cited

U.S. PATENT DOCUMENTS

| | | | |
|---|---|---|---|
| 3,807,878 | 4/1974 | Fields | 250/210 |
| 3,992,113 | 11/1976 | Egli et al. | 356/223 |
| 4,123,171 | 10/1978 | Kato et al. | |
| 4,229,108 | 10/1980 | Childers | |
| 4,473,029 | 9/1984 | Fritz et al. | |
| 4,546,060 | 10/1985 | Miskinis et al. | |
| 4,697,236 | 9/1987 | Butts et al. | |
| 4,750,838 | 6/1988 | DeWolf et al. | |
| 5,519,497 | 5/1996 | Hubble, III et al. | |

OTHER PUBLICATIONS

Scott Edwards, Look Into 'The Eye from TI' For Precision Light Readings, Nov. 96, Stamp Applications No. 21, pp. 1–6.

Texas Instruments, An Evaluation System Interfacing the TSL230/TSL235/TSL245 Light–to–Frequency Converters to a Microcontroller, TSL230EVM User's Guide.

*Primary Examiner*—Stephone B. Allen
*Attorney, Agent, or Firm*—Lawrence P. Kessler

[57] ABSTRACT

An optical densitometer includes a receiver adapted to produce an electrical output voltage characteristic of an optical density to be measured. A voltage-controlled oscillator produces a periodic signal having an output waveform with a frequency and period characteristic of the output voltage of the receiver. A counter produces a digital value corresponding to the output waveform of the periodic signal produced by the oscillator; and a converter produces a digital optical density signal from the digital value. The counter is adapted to produce its digital value corresponding to the frequency or period of the periodic signal produced by the oscillator. The counter may include a portion adapted to produce a digital value corresponding to the frequency of the periodic signal produced by the oscillator; and a portion adapted to produce its digital value corresponding to the period of the periodic signal produced by the oscillator.

7 Claims, 5 Drawing Sheets

DIGITAL DENSITOMETER USING VOLTAGE-CONTROLLED OSCILLATOR, COUNTER, AND LOOK-UP TABLE

CROSS REFERENCE TO RELATED APPLICATIONS

Reference is made to commonly assigned, co-pending U.S. patent application Ser. No. 09/182,912, entitled DIGITAL DENSITOMETER COMBINING AUTO-RANGING WISH CIRCUITRY FOR EXPONENTIAL DECAY, COMPARISON TO A THRESHOLD, AND AN UP-DOWN COUNTER in the names of William A. Hameister and Allen J. Rushing, filed concurrently herewith.

FIELD OF THE INVENTION

The present invention relates to density measurement devices and methods, and is particularly useful in imaging devices such as for example in electrostatographic reproduction apparatus.

BACKGROUND OF THE INVENTION

Control of process conditions in an electrophotographic apparatus can be provided by forming toned density patches on the photoconductors. Such patches are formed by exposing, for example, interframe portions of the photoconductor to exposure light from the imaging source and developing same with the development station under appropriate electrical bias. By measuring the density of the patches, it can be determined whether adjustments are needed to one of the known operating process control parameters such as primary charger setpoint, exposure setpoint, toner concentration, and development bias.

The density of the developed toned patches can be measured using a densitometer. One type, a transmission densitometer, projects light, visible or infrared, through an object onto a photodiode. The amount of energy reaching the photodiode determines the voltage output from the device.

In a copier/printer, the photoconductor passes between the light source and the photodiode. When the photoconductor has toner on the surface, the amount of light reaching the photodiode is decreased. This changes the voltage output from the device, proportional to the amount of light transmitted through the toner on the surface. Based on this voltage, the amount of toner applied to the photoconductor can be varied as required in order to obtain consistent image quality. Another type of densitometer as described in U. S. Pat. No. 5,519,497 uses reflected flux rather than transmitted flux to determine density.

As these machines are used, age of the photoconductor, degradation of the densitometer light emitter, and contamination on surfaces change the voltage output. Typically, the photoconductor is provided with a calibration process to null out the effects of age and contamination, but even so it may be necessary to remove it frequently in order to clean the photodiode or other surfaces.

Many densitometers known from the prior art convert light to density reading using a logarithmic amplifier, which is an expensive device that significantly adds to the cost of the product. There is also prior art that use a look-up table. The output of a normal amplifier is the input to the look-up table. The amplifier output must be converted from analog to digital format before being applied to look-up table.

SUMMARY OF THE INVENTION

It is an object of this invention to provide a new and improved apparatus and method for high resolution density readings over a wide density range.

It is another object of this invention to provide a new and improved apparatus and method for reducing the effect of age and contamination of the photoconductor on a densitometer.

Other objects and advantages of the invention will become apparent from a reading of the specification taken in conjunction with the accompanying drawing.

According to a feature of the present invention, an optical densitometer includes a receiver adapted to produce an electrical output voltage characteristic of an optical density to be measured. A voltage-controlled oscillator produces a periodic signal having an output waveform with a frequency and period characteristic of the output voltage of the receiver. A counter produces a digital value corresponding to the output waveform of the periodic signal produced by the oscillator; and a converter produces a digital optical density signal from the digital value.

According to a preferred embodiment of the present invention, the counter is adapted to produce its digital value corresponding to the frequency or period of the periodic signal produced by the oscillator. The counter may include a portion adapted to produce a digital value corresponding to the frequency of the periodic signal produced by the oscillator; and a portion adapted to produce its digital value corresponding to the period of the periodic signal produced by the oscillator. The converter may include a first portion that produces a digital optical density signal from the digital value corresponding to the frequency of the periodic signal produced by the oscillator; a second portion that produces a digital optical density signal from the digital value corresponding to the period of the periodic signal produced by the oscillator; and means for selecting the output of the first portion of the converter when low densities are being measured and for selecting the output of the second portion of the converter when high densities are being measured.

BRIEF DESCRIPTION OF THE DRAWINGS

The subsequent description of the preferred embodiments of the present invention refers to the attached drawings wherein.

DETAILED DESCRIPTION OF THE INVENTION

Because apparatus of the general type described herein are well known the present description will be directed in particular to elements forming part of, or cooperating more directly with, the present invention. While the invention will be described with reference to imaging apparatus and particularly to an electrophotographic system, the invention can also be used in other imaging apparatus and in environments not in the imaging field.

Figure 1:
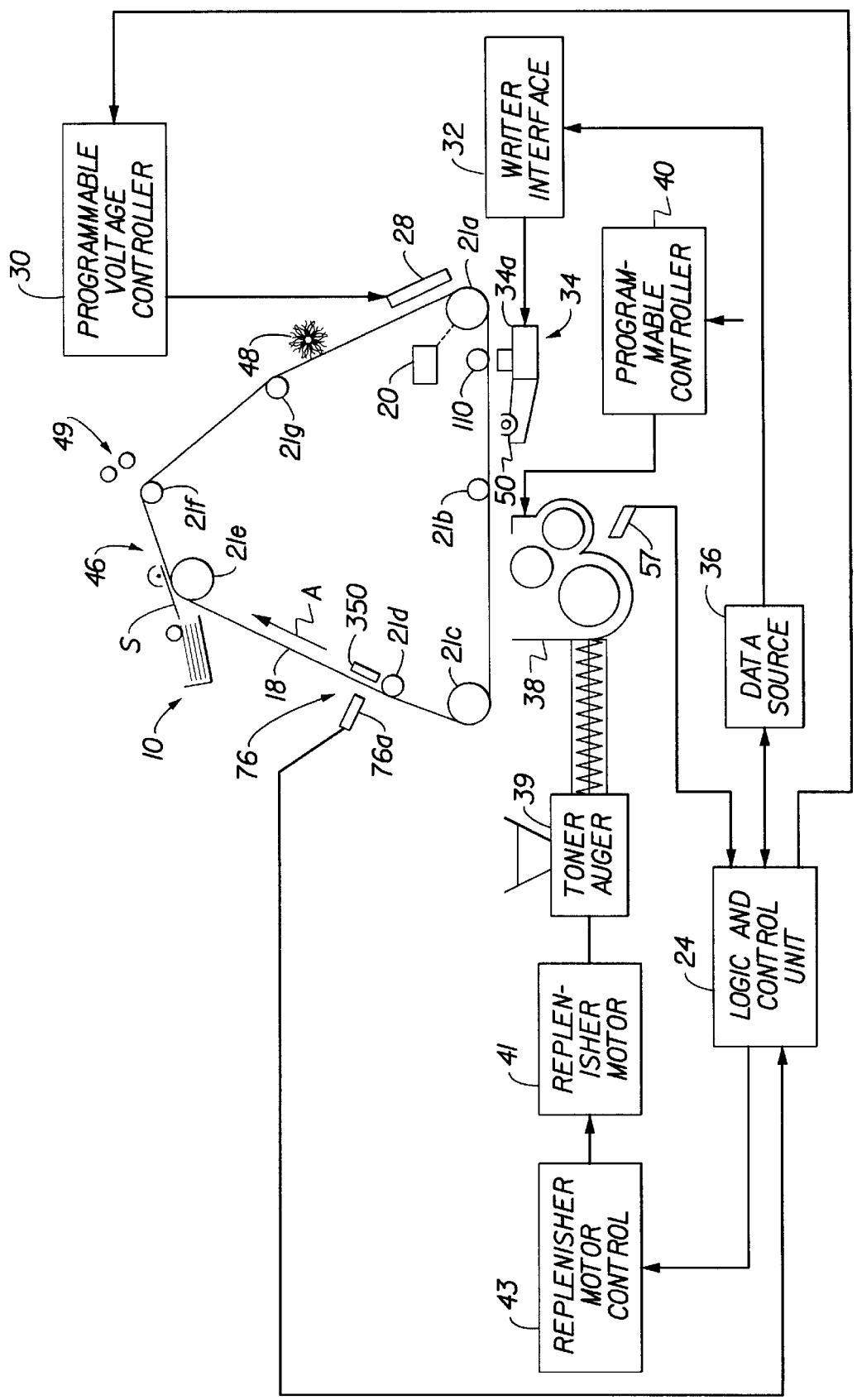
FIG. 1 is a side elevational view in schematic form of an electrostatographic apparatus that is used in accordance with a preferred embodiment of the invention.

With reference to the electrophotographic copier and/or printer machine 10 as shown in FIG. 1, a moving recording member such as photoconductive belt 18 is entrained about a plurality of rollers or other supports 21a–21g one or more of which are driven by a motor 20 so as to advance the belt in a direction indicated by an arrow "A" past a series of work stations of machine 10. A logic and control unit 24, which has a digital computer, has a stored program for sequentially actuating the work stations in response to signals from various sensors and encoders, as is well known.

A primary charging station 28 sensitizes belt 18 by applying a uniform electrostatic charge of predetermined primary voltage $V_0$ to the surface of the belt. The output of the charging station is regulated by a programmable voltage controller 30, which is in turn controlled by logic and control unit 24 to adjust primary voltage $V_0$ for example through control of electrical potential ($V_{grid}$) to a grid that controls movement of corona charges from charging wires to the surface of the recording member, as is well known. Other known forms of chargers, including roller chargers, may also be used.

At an exposure station 34, projected light from a write head 34a dissipates the electrostatic charge on the photoconductive belt to form a latent image of a document to be copied or printed. The write head preferably has an array of light-emitting diodes or other light source such as a laser or other spatial light modulator for exposing the photoconductive belt picture element (pixel) by picture element with a regulated intensity and exposure, $E_O$. Alternatively, the exposure may be by optical projection of an image of a document or a patch onto the photoconductor.

Where a light-emitting diode or other electro-optical exposure source or writer is used, image data for recording is provided by a data source 36 for generating electrical image signals. The data source 36 may be a computer, a document scanner, a memory, a data network, etc. Signals from the data source and/or logic and control unit may also provide control signals to a writer interface 32 for identifying exposure correction parameters in, for example, a lookup table (LUT) for use in controlling image density. Travel of belt 18 brings the areas bearing the latent charge images into a development station 38. The development station has one (more if color) magnetic brushes in juxtaposition to, but spaced from, the travel path of the belt. Magnetic brush development stations are well known. For example, see U.S. Pat. No. 4,473,029 to Fritz et al and U.S. Pat. No. 4,546,060 to Miskinis et al. Other types of development stations may be used as is well known and plural development stations may be provided for developing images in plural colors or with toners of different physical characteristics.

Logic and control unit 24 selectively activates the development station in relation to the passage of the image areas containing latent images to selectively bring the magnetic brush into engagement with or a small spacing from the belt. The charged toner particles of the engaged magnetic brush are attracted imagewise to the latent image pattern to develop the pattern.

Conductive portions of the development station, such as conductive applicator cylinders, act as electrodes. The electrodes are connected to a variable supply of D.C. potential $V_B$ regulated by a programmable controller 40. Details regarding the development station are provided as an example, but are not essential to the invention.

A transfer station 46 as is also well known is provided for moving a receiver sheet "S" into engagement with the photoconductive belt in register with the image for transferring the image to a receiver. Alternatively, an intermediate member may have the image transferred to it and the image may then be transferred to the receiver. A cleaning station 48 is also provided subsequent to the transfer station for removing toner from the belt 18 to allow reuse of the surface for forming additional images. In lieu of a belt, a drum photoconductor or other structure for supporting an image may be used. After transfer of the unfixed toner images to a receiver sheet, such sheet is detacked from the belt and transported to a fuser station 49 where the image is fixed.

The LCU provides overall control of the apparatus and its various subsystems as is well known. Programming commercially available microprocessors is a conventional skill well understood in the art.

Figure 2:
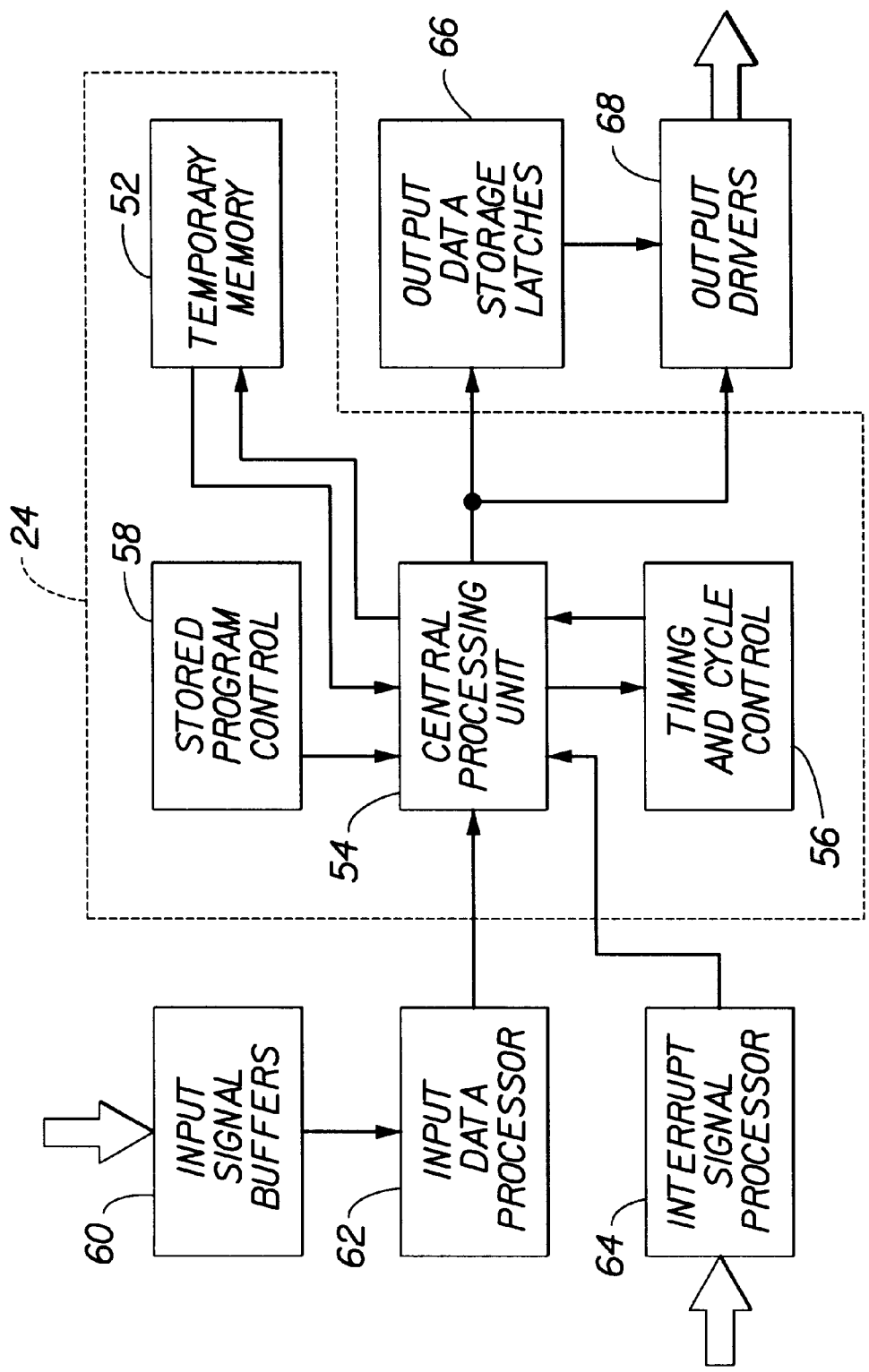
FIG. 2 is a block diagram of a logic and control unit for controlling the apparatus of FIG. 1.

Referring to FIG. 2, a block diagram of a typical LCU 24 is shown. The LCU comprises temporary data storage memory 52, central processing unit 54, timing and cycle control unit 56, and stored program control 58. Data input and output is performed sequentially through or under program control. Input data are applied either through input signal buffers 60 to an input data processor 62 or through an interrupt signal processor 64. The input signals are derived from various switches, sensors, and analog-to-digital converters that are part of the apparatus 10 or received from sources external to machine 10.

The output data and control signals are applied directly or through storage latches 66 to suitable output drivers 68. The output drivers are connected to appropriate subsystems.

Process control strategies generally utilize various sensors to provide real-time control of the electrostatographic process and to provide "constant" image quality output from the user's perspective.

One such sensor may be a densitometer 76 to monitor development of test patches in non-image areas of photoconductive belt 18, as is well known in the art. See for example U. S. Pat. No. 5,649,266. The densitometer is intended to insure that the transmittance or reflectance density of a toned patch on the belt is maintained. The densitometer may be comprised of an infrared emitting diode (IRED) 76a which shines light through the belt or is reflected by the belt onto a photodiode 350. The photodiode generates an electrical signal which varies directly with the flux of light received. The signal is to be converted to a density value reading. In the case of transmission density, this density value is reduced by the density value of a bare patch, to give a signal, $D_{out}$, representative of an estimate of toned density. The $D_{out}$ signal may be used to adjust process parameters $V_0$, $E_0$, or $V_B$. The $D_{out}$ signal may also be used to assist in the maintenance of the proper concentration of toner particles in the developer mixture by having the LCU provide control signals to a replenisher motor control 43. Replenisher motor control 43 controls replenisher motor 41 that in turn drives a toner auger 39 for feeding new toner particles into development station 38. A toner concentration monitor probe 57 provides signals to the LCU about relative concentration of toner particles to carrier particles in the developer mix.

A second sensor useful for monitoring process parameters is an electrometer probe 50 which is mounted at a location preferably downstream of the corona charging station 28 relative to the direction of the movement of the belt 18 which direction is indicated by the arrow A. In the example illustrated in FIG. 1 the electrometer probe 50 is mounted immediately downstream of the writehead 34a.

Figure 3:
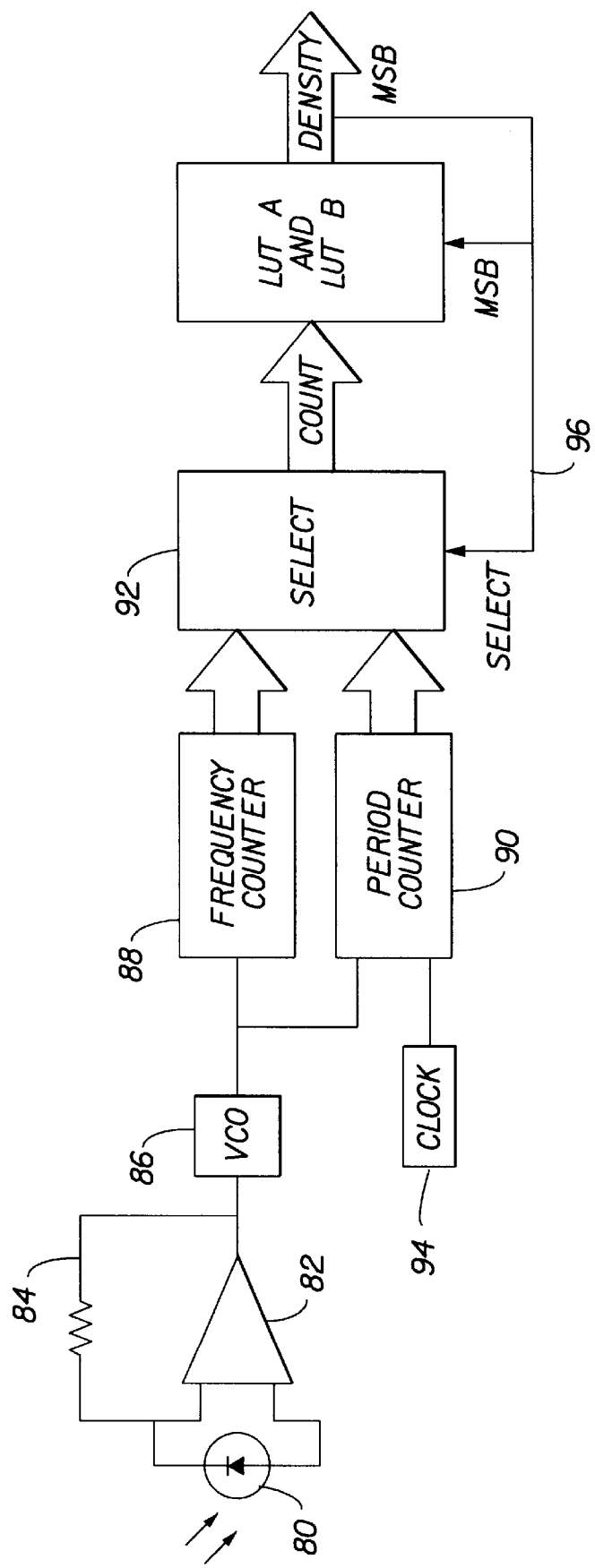
FIG. 3 is a block diagram of a densitometer according to a preferred embodiment of the present invention.

Referring to FIG. 3, a receiver includes a conventional photodiode detector 80 and an amplifier 82. A resistor 84 over amplifier 82 provides a predetermined gain so that the receiver outputs a voltage signal that is proportional to the photocurrent in photodiode detector 80. The output of the receiver goes into a voltage-controlled oscillator (VCO) 86. VCO produces a voltage output that oscillates at a frequency proportional to the input voltage. Preferably, the VCO output is a square wave. The VCO output is inputted to two different counters 88 and 90. Counter 88 is a frequency counter, and counter 90 is a period counter.

Frequency counter 88 counts the number of oscillations of the VCO output during a predetermined time period, and outputs the count to a select unit 92. In contrast, period counter 90 uses the VCO output to determine an interval during which the output of a fixed frequency clock 94 is counted, and outputs the count to select unit 92. In a sense, period counter 90 measures a period of the VCO during which period it counts a series of clock pulses. The VCO turns the period counter ON and OFF. It resets and starts it over with a new count on every period of the VCO output. Select unit 92 is adapted to transmit either the output of frequency counter 88 or period counter 90 to one of a pair of look-up tables "A" and "B", respectively; depending on the condition of a select signal 96.

It is best to select the output of frequency counter 88 for transmission to look-up table "A" when the light intensity is high (corresponding to low densities). Under those conditions, the output frequency of VCO 86 is high, and the high frequency pulses are counted to get a large count over a fixed time interval. This results in a very high resolution at this end of the graph of FIG. 4.

Figure 4:
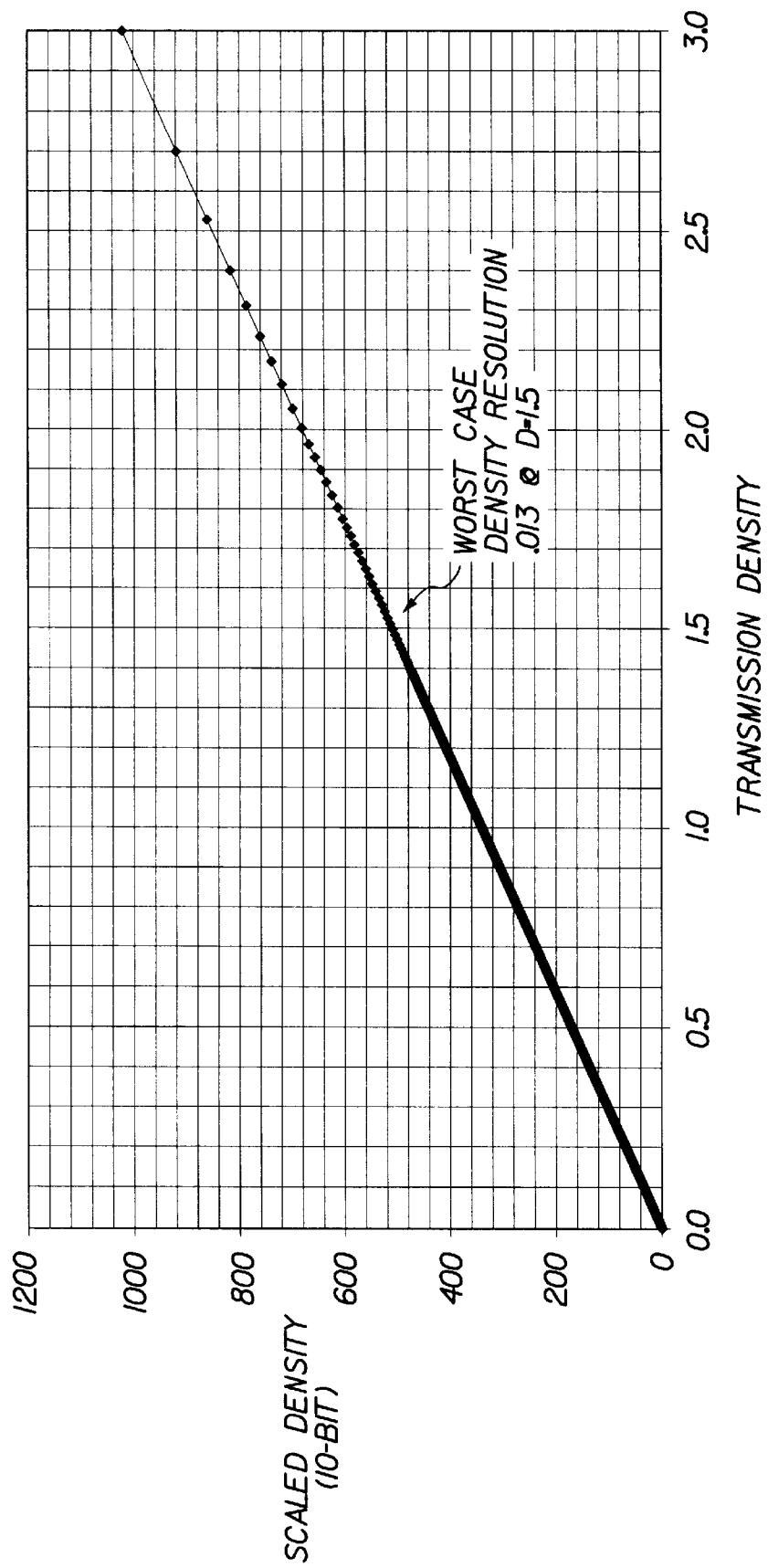
FIG. 4 is a graph of density readings according to a frequency counter portion of the densitometer of FIG. 3.
Figure 5:
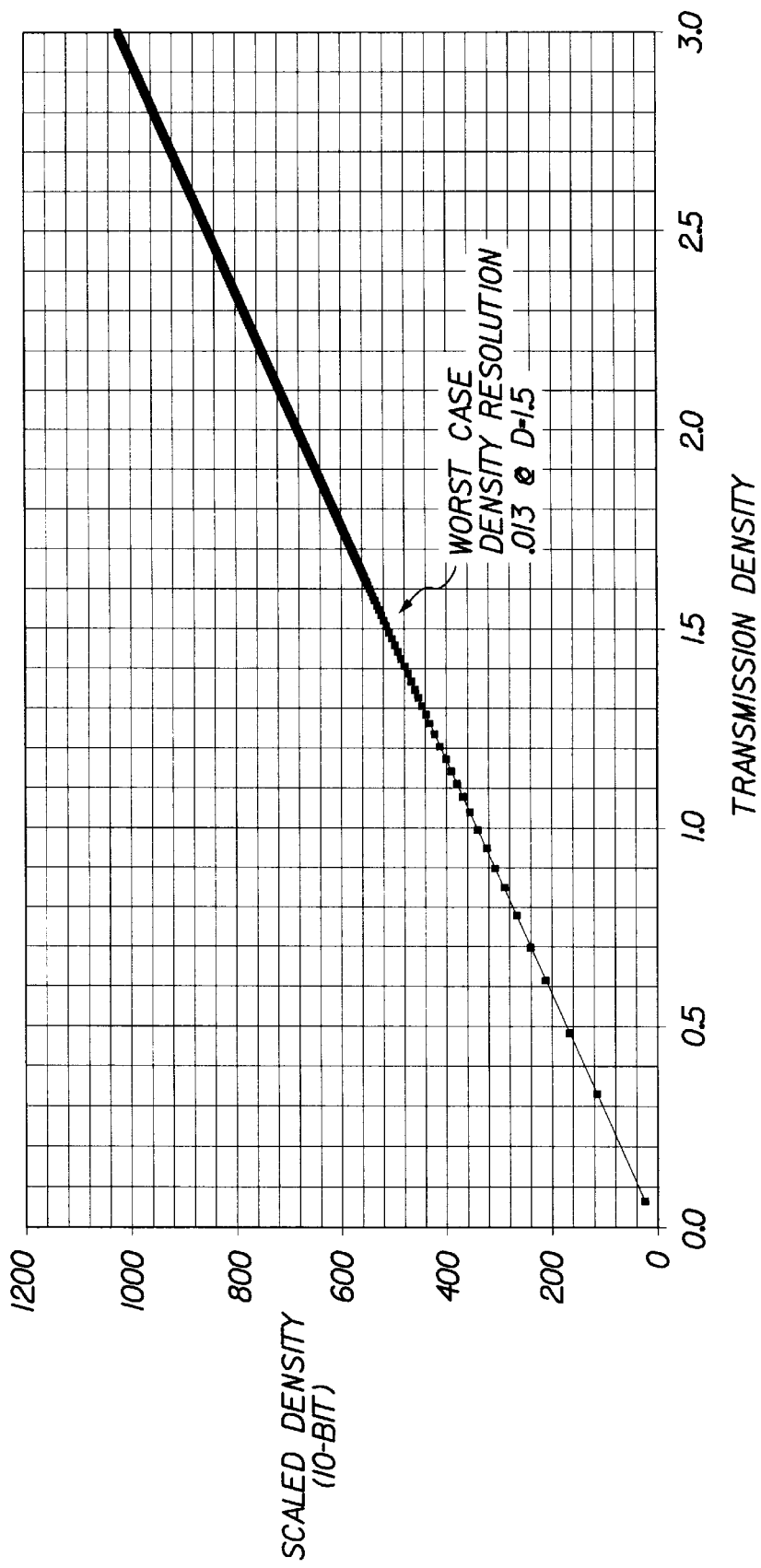
FIG. 5 is a graph of density readings according to a period counter portion of the densitometer of FIG. 3.

If the light intensity is low, as is the case when a high density is being measured, the output frequency of VCO 86 is low. When the VCO output frequency is low, only a few pulses are counted in a fixed time interval. This is illustrated at the upper (right hand) end of the graph of FIG. 4. This would result in poor density resolution. The remedy is to use period counter 90 for high density measurements, where the VCO frequency is very slow. Now, the same kind of chart (FIG. 5) for the period counter is just the reverse of the frequency counter chart (FIG. 4), in that there is greater resolution at the upper (right hand) end and poor resolution at lower (left hand) end. Whereas the frequency counter gives us a high resolution density output on the left hand side of FIG. 4 where the density is low, the period counter provides good resolution at the right hand side of FIG. 5, where the density is highest. According to a feature of the present invention, one counter is utilized for one portion of the density scale and the other counter is utilized for the other portion of the density scale to get good resolution over the entire density range. For 10-bit counters and a 10-bit LUT output, as illustrated in FIGS. 4 and 5, the combined worst-case resolution (0.013 density units) occurs in the middle of the 0.0 to 3.0 density range, as shown in the drawings.

The invention has been described in detail with particular reference to certain preferred embodiments thereof, but it will be understood that variations and modifications can be effected within the spirit and scope of the invention.

What is claimed is:

1. An optical densitometer comprising:
   a receiver which is adapted to produce an electrical output voltage characteristic of an optical density to be measured;
   an oscillator adapted to produce a periodic signal having an output waveform with a frequency and period characteristic of the output voltage of the receiver;
   a counter that produces a digital value corresponding to the output waveform of the periodic signal produced by the oscillator, said counter including (i) a portion adapted to produce a digital value corresponding to the frequency of the periodic signal produced by the oscillator and (ii) a portion adapted to produce its digital value corresponding to the period of the periodic signal produced by the oscillator; and
   a converter that produces a digital optical density signal from the digital value.

2. An optical densitometer as defined in claim 1, wherein the converter includes:
   a portion that produces a digital optical density signal from the digital value corresponding to the frequency of the periodic signal produced by the oscillator; and
   a portion that produces a digital optical density signal from the digital value corresponding to the period of the periodic signal produced by the oscillator.

3. An optical densitometer as defined in claim 1, wherein the converter includes:
   a first portion that produces a digital optical density signal from the digital value corresponding to the frequency of the periodic signal produced by the oscillator;
   a second portion that produces a digital optical density signal from the digital value corresponding to the period of the periodic signal produced by the oscillator; and
   means for selecting the output of the first portion of the converter when low densities are being measured and for selecting the output of the second portion of the converter when high densities are being measured.

4. An optical densitometer as defined in claim 1, wherein the oscillator is a voltage-controlled oscillator.

5. A process for measuring an optical density, said process comprising:
   producing an electrical output voltage characteristic of an optical density to be measured;
   producing a periodic signal having an output waveform with a frequency and period characteristic of the output voltage of the receiver;
   producing a digital value corresponding to the output waveform of the periodic signal, said digital value having (i) a portion corresponding to the frequency of the periodic signal; and (ii) a portion corresponding to the period of the periodic signal; and
   producing a digital optical density signal from the digital value.

6. A process for measuring an optical density as defined in claim 5, wherein the step of producing the digital optical density signal includes:
   producing a digital optical density signal from the digital value corresponding to the frequency of the periodic signal; and
   producing a digital optical density signal from the digital value corresponding to the period of the periodic signal.

7. A process for measuring an optical density as defined in claim 5, wherein the step of producing the digital optical density signal includes:
   producing a digital optical density signal from the digital value corresponding to the frequency of the periodic signal;
   producing a digital optical density signal from the digital value corresponding to the period of the periodic signal; and
   selecting the digital optical density signal from the digital value corresponding to the frequency of the periodic signal when low densities are being measured and for selecting the digital optical density signal from the digital value corresponding to the period of the periodic signal when high densities are being measured.

* * * * *